United States Patent [19]

Henkin

[11] 4,210,137

[45] Jul. 1, 1980

[54] ALTITUDE CONDITIONING METHOD AND APPARATUS

[76] Inventor: Melvyn L. Henkin, 5011 Donna Ave., Tarzana, Calif. 91356

[21] Appl. No.: 901,621

[22] Filed: May 1, 1978

Related U.S. Application Data

[63] Continuation-in-part of Ser. No. 646,424, Jan. 5, 1976, Pat. No. 4,086,923.

[51] Int. Cl.² ............................................. A61M 16/00
[52] U.S. Cl. ............................ 128/200.24; 128/205.29
[58] Field of Search ................ 128/185, 205, 204, 208, 128/209, 210, 211, 145 R, 2.08, 2 C, 2.07, 202, 203, 184, 142 R, 145.6, 145.8, 147, 191 R, 201, 142.2, 145 A, 25 R, 33, 24 R; 272/99 R

[56] References Cited

U.S. PATENT DOCUMENTS

| | | | |
|---|---|---|---|
| 2,227,536 | 1/1941 | D'Agostino | 128/192 |
| 2,844,145 | 7/1958 | Berge | 128/147 |
| 3,455,294 | 7/1969 | Adler et al. | 128/25 R |
| 3,513,843 | 5/1970 | Exler | 128/202 |
| 4,086,923 | 5/1978 | Henkin | 128/140 R |

FOREIGN PATENT DOCUMENTS

1021191  2/1953  France ................................. 128/2.08

*Primary Examiner*—Henry J. Recla
*Attorney, Agent, or Firm*—Freilich, Hornbaker, Wasserman, Rosen & Fernandez

[57] ABSTRACT

An improved breathing method and apparatus for enabling a user, while at low altitude, e.g. sea level, to acclimate himself to high altitude conditions. The apparatus includes an inspiratory tube and an expiratory tube and means for selectively mixing a certain portion of oxygen-reduced expired air with ambient air to supply air for inspiration. The first ends of the inspiratory and expiratory tubes are coupled to a mouth and/or nose breathing mask. The remote end of the expiratory tube is coupled through a proportioning means to the environment and to a reservoir or air storage chamber. The remote end of the inspiratory tube is also coupled to the proportioning means so as to pull ambient air from the environment, as well as oxygen-reduced air from the reservoir. By varying the proportioning means, the ratio of ambient air to expired air, and thus the oxygen concentration of the inspired air, is varied so as to enable the user to select the particular elevated altitude to be simulated. Means are included for adjusting the range over which said proportioning means can be varied. Means are also included for adjusting the proportion of expired air which is caused to flow through $CO_2$ absorber material prior to being inspired.

17 Claims, 8 Drawing Figures

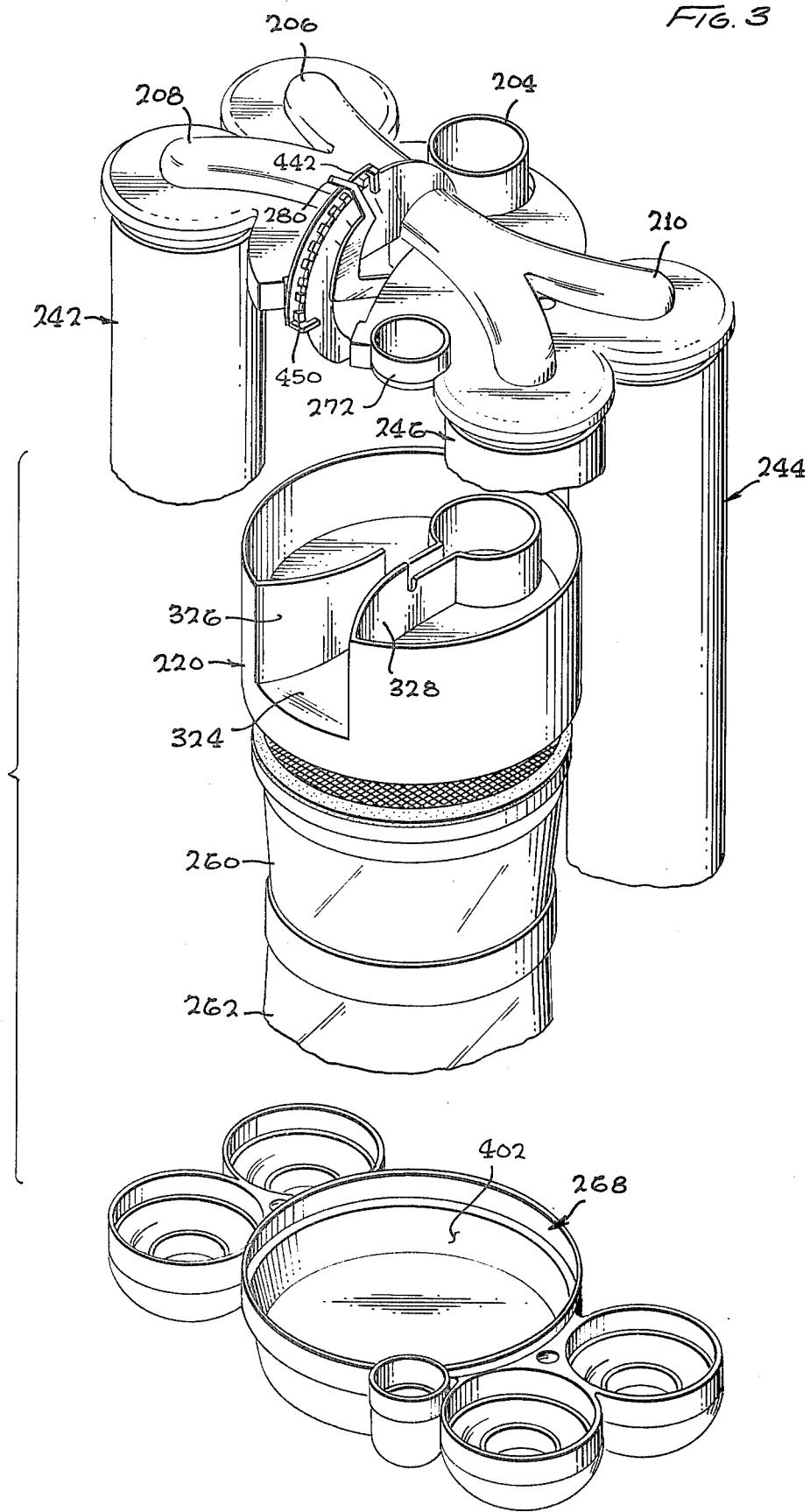

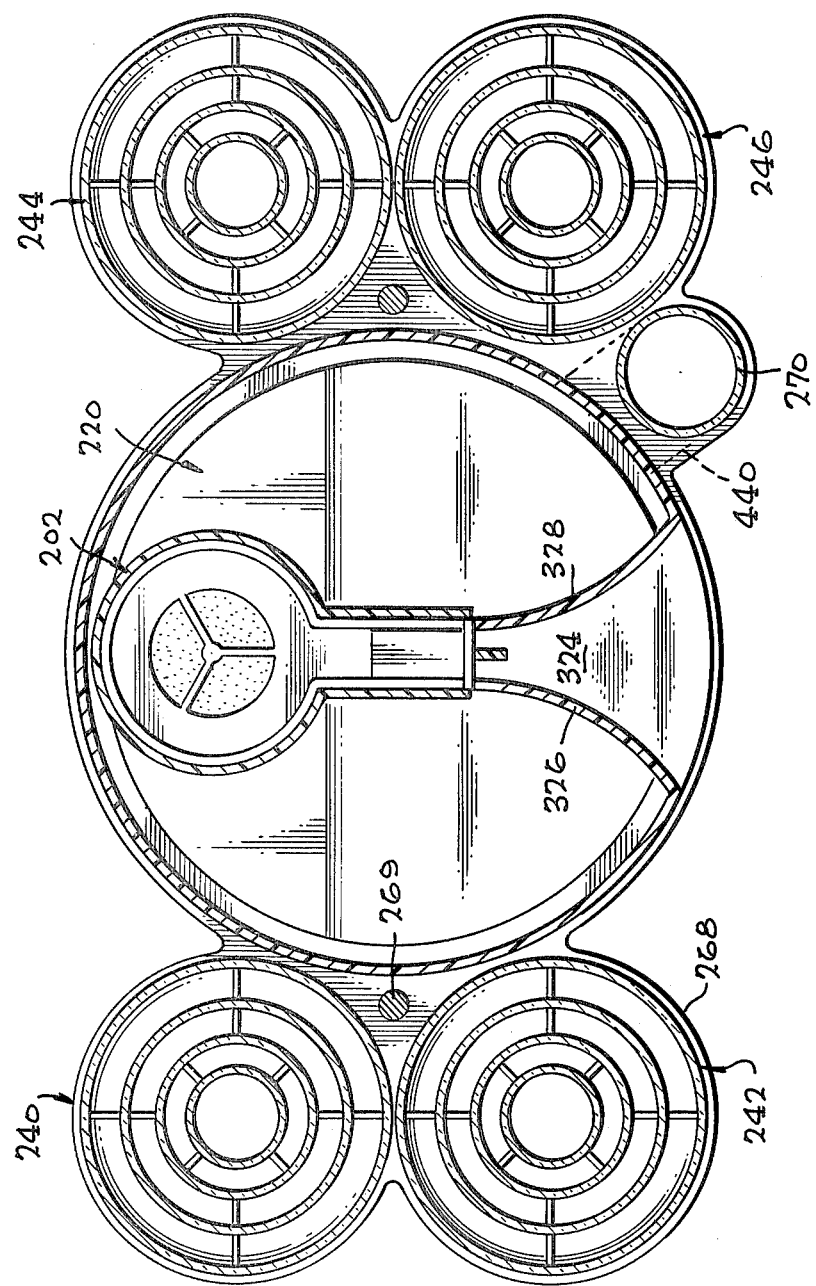

ALTITUDE CONDITIONING METHOD AND APPARATUS

RELATED APPLICATIONS

This application is a continuation-in-part of U.S. application Ser. No. 646,424 filed Jan. 5, 1976 now U.S. Pat. No. 4,086,923.

BACKGROUND OF THE INVENTION

This invention relates generally to an improved breathing method and apparatus for supplying air to a user having a lower partial pressure of oxygen ($PO_2$) than the ambient air so as to simulate an elevated altitude.

Persons who ordinarily function at a near-sea-level altitude frequently experience headache, shortness of breath, nausea, sleeplessness, and reduced endurance during the initial days at higher altitude, e.g. above 7,500 feet. These factors are, in large part, attributable to the diminishing amount of oxygen available as altitude increases. A typical situation involves a sea-level resident who occasionally takes a skiing weekend above 7,500 feet. As altitude increases, oxygen availability diminishes, thus requiring the person to breathe deeper in an effort to supply sufficient oxygen to his bloodstream. The partial pressure of oxygen ($PO_2$) at 7,500 feet is only 75% (of the $PO_2$ at sea level) and at 10,000 feet is only 65%. At 19,000 feet, the $PO_2$ is only 50%, thus meaning that a unit volume of air at 19,000 feet contains only half as much oxygen as that same unit volume at sea level. Typically, after a few days at the higher altitude, the person will become acclimated and the aforementioned problems subside. Interestingly, evidence suggests that persons who experience high altitudes on a frequent and regular basis appear to maintain a certain degree of acclimation to the altitude and are considerably better able to avoid the aforementioned problems than infrequent visitors.

Applicant's parent application discloses a breathing method and apparatus for enabling a user, while at low altitudes, e.g. sea level, to acclimate himself to high altitude conditions.

In the preferred embodiment disclosed in Applicant's parent application, first ends of inspiratory and expiratory tubes are coupled to a mouth and/or nose breathing mask. The remote end of the expiratory tube is coupled through a proportioning means to the environment and to a reservoir or air storage chamber. The remote end of the inspiratory tube is also coupled to the proportioning means so as to pull ambient air from the environment, as well as oxygen depleted air from the reservoir. By varying the proportioning means, the ratio of ambient air to expired air, and thus the oxygen concentration of the inspired air, is varied so as to enable the user to select a particular elevated altitude to be simulated. In order to accommodate users having different tidal volumes and rates, a large capacity reservoir sufficient to accommodate the largest tidal volume user is provided. Carbon dioxide ($CO_2$) absorber material is incorporated in the system to remove $CO_2$ from the air drawn from the reservoir for inspiration by the user.

In use, a person may breathe through the apparatus for approximately 30-60 minutes per day, gradually increasing the elevation of the simulated altitude in increments of 2,000 to 3,000 feet, as he becomes acclimated to each altitude. Evidence of acclimation is indicated by only a small increase in pulse rate measured while performing mild exercise. In addition to enabling a user to become acclimated to higher altitudes, the method and apparatus disclosed in Applicant's parent application is useful for other purposes such as to increase endurance of competing athletes. That is, endurance during competition while breathing a certain $PO_2$ will be enhanced by training while breathing a lower $PO_2$.

SUMMARY OF THE INVENTION

The present invention is directed to an improved method and apparatus for supplying air to a user having a lower partial pressure of oxygen ($PO_2$) than the ambient air. These improvements are primarily directed toward (1) discouraging a user from inadvertently simulating a higher altitude than he is prepared for, (2) enhancing the smoothness of air flow into and out of the reservoir and minimizing mixing between air entering the reservoir and previously stored air, and (3) enabling the user to regulate the $CO_2$ content of inspired air.

More particularly, in accordance with one aspect of the invention, means are provided for selectively adjusting the range of altitudes which can be simulated. In the preferred embodiment, an adjustably mounted toothed rack is provided which defines a plurality of detent positions for the valve element which determines the proportions of the inspired air derived from the reservoir and from the environment. When the rack is set in certain positions, it limits the range over which the proportioning valve element can be varied to thus limit the maximum altitude which can be simulated.

In accordance with a further aspect of the preferred embodiment, separate multiple reservoirs are provided coupled in parallel fashion in the air flow path. A manifold subassembly is coupled to the user's expiratory path and distributes a portion of the user's expired air to the multiple reservoir entrance openings. Each reservoir defines a plurality of flow path segments communicating with one another to form a series flow path extending from the entrance opening to an overflow opening. The flow path defined by the manifold subassembly, as well as the reservoir flow path segments, are of increasing cross-sectional area in the direction of expired air flow to thus minimize flow resistance.

In accordance with a still further aspect of the invention, means are provided for regulating the $CO_2$ content of the air inspired by the user by incorporating in the preferred embodiment a flow path which bypasses the $CO_2$ absorber material. Valve means are included for selectively establishing the proportions of inspired air which pass through and which by-pass the $CO_2$ absorber material. The capability of controlling the amount of $CO_2$ is particularly useful in some medical procedures where it is desired that the $CO_2$ content of inspired air remain at a certain level.

BRIEF DESCRIPTION OF THE FIGURES

FIG. 3 is an exploded perspective view of the preferred embodiment depicted in FIG. 2;

FIG. 4 is a top plan view, partially broken away, of the apparatus of FIG. 2;

FIG. 5 is a horizontal sectional view along the plane just below the manifold subassembly of FIG. 2;

DESCRIPTION OF THE PREFERRED EMBODIMENTS

Figures 1, 8:
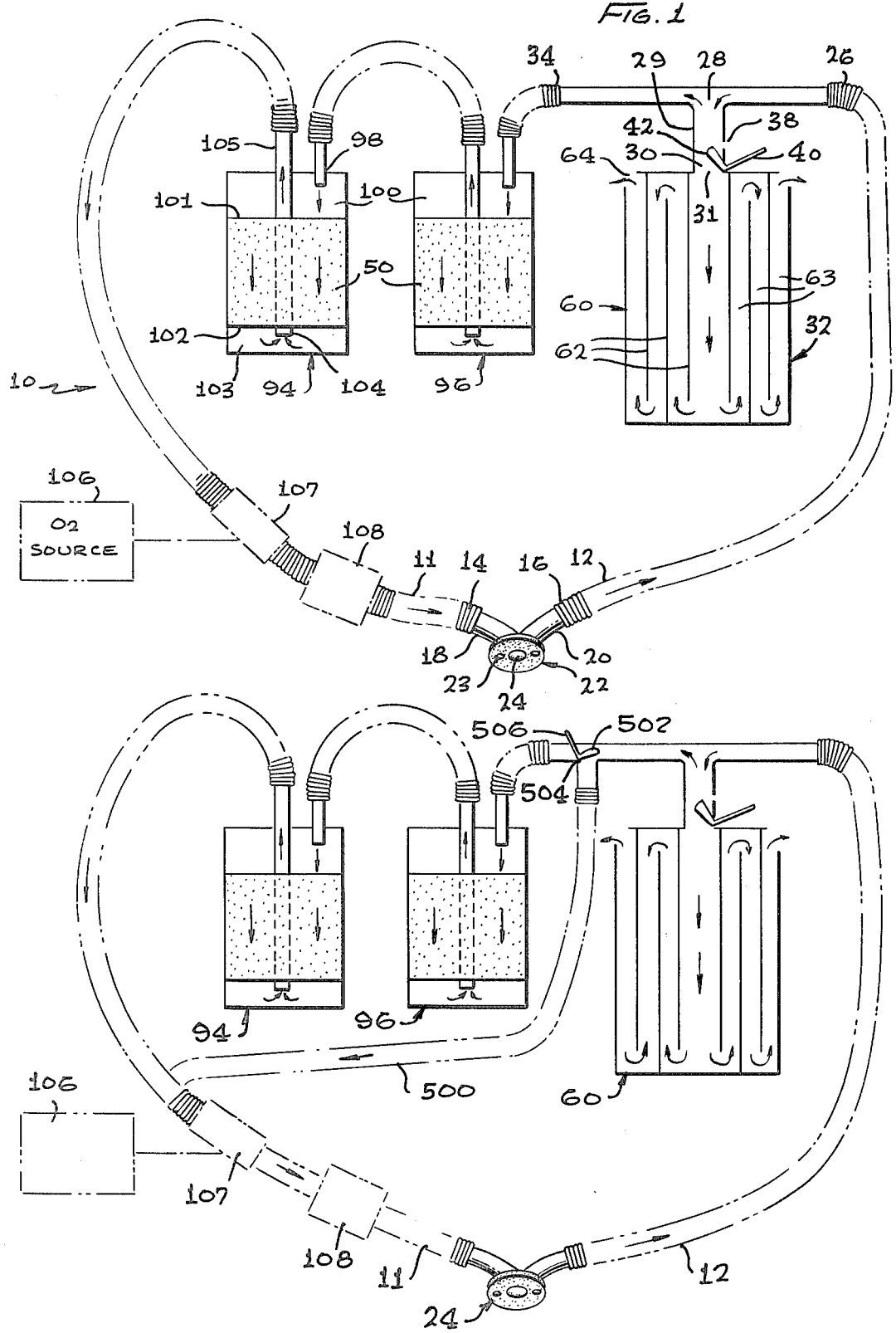
FIG. 1 is a schematic diagram of a breathing apparatus, as disclosed in Applicant's parent application, showing the direction of air flow through the inspiratory and expiratory tubes and reservoir means.
FIG. 8 is a schematic diagram of an alternative breathing apparatus in accordance with the present invention.

Attention is now directed to FIG. 1 which schematically illustrates a breathing apparatus 10 in accordance with the invention disclosed in Applicant's parent application for conditioning a user to the low oxygen conditions found at high altitudes. The user is able to condition himself to the low oxygen at high altitudes by breathing through the apparatus depicted in FIG. 1 for limited intervals for each day over an extended period of time. The apparatus of FIG. 1 supplies air for inspiration by the user whose oxygen content can be selectively varied to simulate virtually any altitude above ambient up to a physiologically safe level.

Briefly, apparatus in accordance with the invention as described in said parent application functions to store expired, oxygen-depleted air, in a reservoir and to mix this oxygen depleted air with ambient air to supply air for inspiration. By varying the proportion of ambient air mixed with oxygen depleted air from the reservoir, the oxygen concentration of the inspired air, and thus the altitude simulated, can be varied.

The exemplary system 10 in FIG. 1 is comprised of an inspiratory tube 11 and an expiratory tube 12 (preferably formed of conventional corrugated tubing similar to that used in anesthesia delivery systems) each having their first ends, 14 and 16 respectively, coupled to nipples 18 and 20 of a patient mouth piece 22, illustrated as including a port 24 for communicating with a user's air channel through his mouth. However, it should be understood that a nose or full face mask can be utilized in the alternative.

The expiratory tube 12 terminates at a second end 26 and includes a one-way expiratory valve mounted therein for restricting air flow from the first end 16 to the second end 26 of the tube 12. The second end 26 of the expiratory tube 12 opens into entrance opening 28 of pipe section 29. Pipe section 29 includes a second opening 30 which communicates with the entrance opening 31 of a reservoir or air storage chamber 32. The entrance opening 28 of pipe section 29 also communicates with a second end 34 of the inspiratory tube 11. A one-way check valve is incorporated in the inspiratory tube 11 for restricting air flow therein from the second end 34 to the first end 14 of the tube 11.

The pipe section 29, in addition to opening into the reservoir 32, opens to the environment through port 38. A proportioning valve mechanism 40 is mounted in the pipe section 29 and includes a baffle 42 for varying the air flow path dimensions between the paths from pipe section entrance opening 28 to the environment through the port 38 and to the reservoir 32 through opening 30. That is, in a first extreme position of the proportioning valve mechanism 40, the pipe section entrance opening 28 communicates primarily with the ambient air environment through port 38, and in the opposite extreme position, communicates primarily through the opening 30 to the reservoir 32.

Carbon dioxide ($CO_2$) absorber material 50 is incorporated in the inspiratory tube 11 for removing carbon dioxide from the air flowing from the second end 36 to the first end 14 of inspiratory tube 11.

In the use of the apparatus of FIG. 1, a user would grip the studs 23 of mouth piece 22 between his teeth so as to communicate the opening 24 with the user's air channel through his mouth. The user would then breathe through his mouth in normal fashion for a certain interval of time, e.g. 30-60 minutes. On each expiration, the expired air flows through the tube 12 from the first end 16 to the second end 26 thereof and into pipe section 29. A portion of the expired air will be exhausted through port 38 to the environment. The remaining portion of the expired air will enter the reservoir 32 through pipe section opening 30 and be stored therein. On inspiration, the user will pull air into the second end 34 of inspiratory tube 11 from the environment through port 38 and from the reservoir 32 through pipe section opening 30. The air pulled from the reservoir 32 will, of course, have a lower oxygen concentration than the ambient air pulled through port 38 from the environment. By varying the position of proportioning baffle 42, the oxygen concentration of the air to be inspired by the user can be caused to be either closer to that of the oxygen depleted expired air stored in reservoir 32 or closer to that of the ambient air available through port 38. As depicted in FIG. 1, the air drawn into the inspiratory tube is steered through the $CO_2$ absorber material 50 in order to remove therefrom the carbon dioxide contained in the expired air drawn from the reservoir 32. This air then flows through the inspiratory tube 11 to the first end 14 and is inspired by the user.

Now considering the system of FIG. 1 in greater detail, it should be recognized that the total volume of air expired on each breath by a user is divided into two variable portions; the first portion exits through port 38 and dissipates in the environment and the second portion enters the reservoir 32. It is important that the reservoir 32 have a sufficient capacity to be able to supply enough oxygen depleted air during the inspiration phase to reduce the amount of oxygen in the inspired air to correspond to the maximum altitude it is desired to simulate. Although in the preferred embodiment disclosed herein, this maximum altitude will be assumed to be 19,000 feet above sea level, it should be understood that an apparatus in accordance with the invention can be dimensioned so as to be limited to any desired maximum altitude. It is preferable that the reservoir have a capacity of about four liters in order to enable virtually the largest tidal volume user to simulate the maximum altitude (assumed to be approximately 19,000 feet).

On an inspiration phase of tidal volume equal to the tidal volume of the prior expiration, all of the expired air stored in the reservoir 32 reverses direction and flows into the inspiratory tube 11. Additionally, a volume of ambient air equal to the volume of expired air, expelled through the port 38 on expiration, is drawn into the inspiratory tube to be mixed with the expired air drawn from the reservoir 32 to create a total volume of air to be inspired equal to the volume previously expired. It is preferable that the reservoir 32 be designed so as to permit easy flow of the air into and out of it so as to avoid introducing any resistance to the user's breathing. Moreover, it is desirable that the air flowing into the reservoir merely push ahead the air already in the reservoir without mixing with it. This will assure that the air retrieved from the reservoir during each inspiration phase consists of the air stored in the reservoir during the immediately preceding expiration phase combined with some ambient air.

To assure smooth non-turbulent non-mixing air flow, the reservoir 32 is comprised of a cylindrical housing 60 containing a plurality of spaced vertical cylindrical baffles 62 concentrically arranged to define a central cylindrical volume surrounded by toroidal volumes 63 of increasing radius. The baffles are dimensioned so as to define a series air flow path through the respective volumes. That is, as can be seen in FIG. 1, the pipe section 29 opens into housing entrance opening 30 communicating with the aforementioned central volume. This central volume is defined by the smallest radius baffle 62 whose lower edge is spaced from the bottom of housing 60 so as to permit air flow to or from the immediately surrounding toroidal volume. Note that the space between the baffles 62 and housing 60 is alternated between the baffle lower and upper edges to thereby define a series air flow path extending from entrance opening 30 toward overflow opening 64. The housing is open to the environment at 64 to permit the air in the housing to be pushed out ahead of newly expired air entering the housing via entrance opening 30, thus avoiding the buildup of back pressure which would make breathing difficult.

In use, on each expiration, expired air is exhausted into the cylindrical housing 60 and stored within the series coupled volumes defined by baffles 62. On the subsequent inspiration, the stored air is retrieved flowing in a direction from the overflow opening 64 toward the entrance opening 30.

The proportioning valve mechanism 40 is comprised of a baffle 42 mounted for pivotal movement to vary the ratio of air flow between the reservoir and the environment. The range of movement of the baffle 42 is limited so as to prevent complete closure of the flow path to the environment. That is, when used close to sea level, the extreme closed position of baffle 42 still assures sufficient air flow to and from the environment to limit the altitude simulated to 19,000 feet. FIG. 1 illustrates the utilization of two separate cannisters 94 and 96 of $CO_2$ absorber material 50. Each cannister includes an air entrance opening 98 which communicates with an upper air chamber 100. The $CO_2$ absorber material 50 is retained between an upper apertured plate 101 and a lower apertured plate 102. Air flow is from the upper chamber 100 through the upper plate 101, through the $CO_2$ absorber material 50, and through the lower plate 102 to a lower air chamber 103. The air then flows through the chamber 103 through a central pipe section 104 to the air exit opening 105.

FIG. 1 further illustrates (by dashed line) devices which may be optionally incorporated in the system to make it more suitable for particular applications. For example only, it has now been recognized that apparatus in accordance with the present invention may prove quite useful for evaluating pathological cardiac deficiencies by subjecting a user to an oxygen reduced concentration or simulated high altitude, and monitoring his vital signs and EKG. Where the apparatus is used in such an application, it is desirable to provide means for rapidly administering supplemental oxygen into the inspiratory tube 11 in the event the user experiences difficulties at the altitude setting of the device. Accordingly, FIG. 1 illustrates an oxygen source 106 coupled by a valve mechanism 107 to the inspiratory tube 11. It is contemplated, of course, that apparatus of the type shown in FIG. 1 for the aforementioned application to evaluate pathological cardiac conditions would be used only under the care of an attending physician.

As a still further variation, it may be desirable to incorporate an oxygen sensing meter 108 in the inspiratory tube 11 to accurately measure inspired oxygen concentrations. It is not contemplated that such a measurement be desirable in typical applications of the present invention but, indeed, it may be desirable in certain situations to enable the verification of the simulated altitude.

Attention is now called to FIGS. 2-7 which illustrate a preferred embodiment of the invention schematically illustrated in FIG. 1. The improved apparatus depicted in FIGS. 2-7 is comprised of the following major members:

(1) The manifold subassembly 202 which includes a nipple 204 for receiving the second or remote end of the expiratory tube 12 (FIG. 1). Additionally, the manifold subassembly 202 defines four passageways 206, 208, 210 and 212 for distributing expired air entering the nipple 204 to the multiple reservoirs.

(2) An air mixing chamber member 220 which cooperates with the previously mentioned manifold subassembly 202 to form an air mixing chamber for receiving the expired air entering the nipple 204 of manifold subassembly 202. The air mixing chamber communicates through a proportioning valve means with the environment and with the four previously-mentioned passageways 206, 208, 210, and 212 in the manifold subassembly 202.

(3) Four separate reservoir members 240, 242, 244, and 246 are arranged to communicate respectively with passageways 206, 208, 210 and 212 in the manifold subassembly 202.

(4) First and second $CO_2$ absorber cannisters 260, 262 are provided for passing air stored in the reservoirs to remove carbon dioxide therefrom.

(5) A base member 268 is provided which is coupled to the manifold subassembly 202 by a suitable fastening means 269 and which sandwiches the reservoirs and $CO_2$ absorber cannisters therebetween, as well as providing an air flow path from the $CO_2$ absorber cannisters to a tube 270 which terminates in nipple 272 adapted to be coupled to the inspiratory tube 11 of FIG. 1.

Prior to considering the detailed structure of the preferred embodiment illustrated in FIGS. 2-7, an overall summary of the operation and flow pattern of the apparatus will be described. During an expiration phase, the user's expired air will enter nipple 204 flowing past a one-way check valve. The expired air will then enter an air mixing chamber defined between the manifold subassembly 202 and the air mixing chamber member 220. From the air mixing chamber, a portion will flow to the environment while another portion will flow into the manifold passageways 206, 208, 210 and 212. The proportioning between the air flow to the environment and into the manifold passageways is determined by the setting of the proportioning valve member 280. The expired air flowing into the passageways 206, 208, 210 and 212 will then flow into the reservoirs 240, 242, 244, 246 and be stored therein. On inspiration, a negative pressure will be formed in the inspiratory tube 11. This will cause the air previously stored in the reservoirs to be drawn up into the passageways 206, 208, 210 and 212 and into the air mixing chamber defined between the subassembly 202 and the mixing chamber member 220. Additionally, again depending upon the setting of the proportioning valve member 280, air will be drawn from the environment into the air mixing chamber to be mixed with the air retrieved from the reservoirs. This combined air will then be drawn downwardly through the $CO_2$ absorber cannisters 260 and 262 and thence into the bottom of the tube 270 and then up through the nipple 272 and into the inspiratory tube 11 for delivery to the user.

Figure 2:
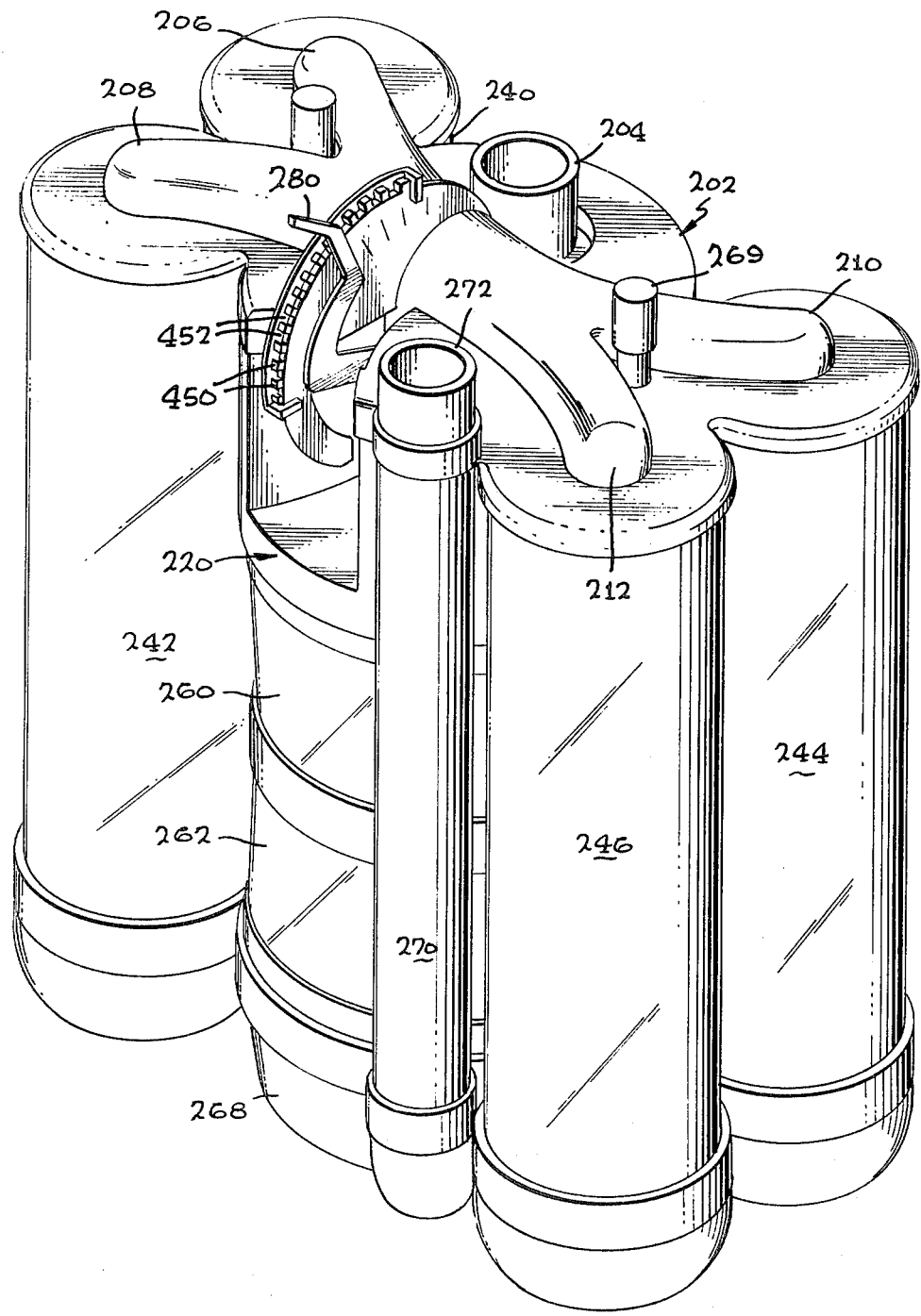
FIG. 2 is a perspective view of a preferred embodiment of the present invention.
Figure 9:
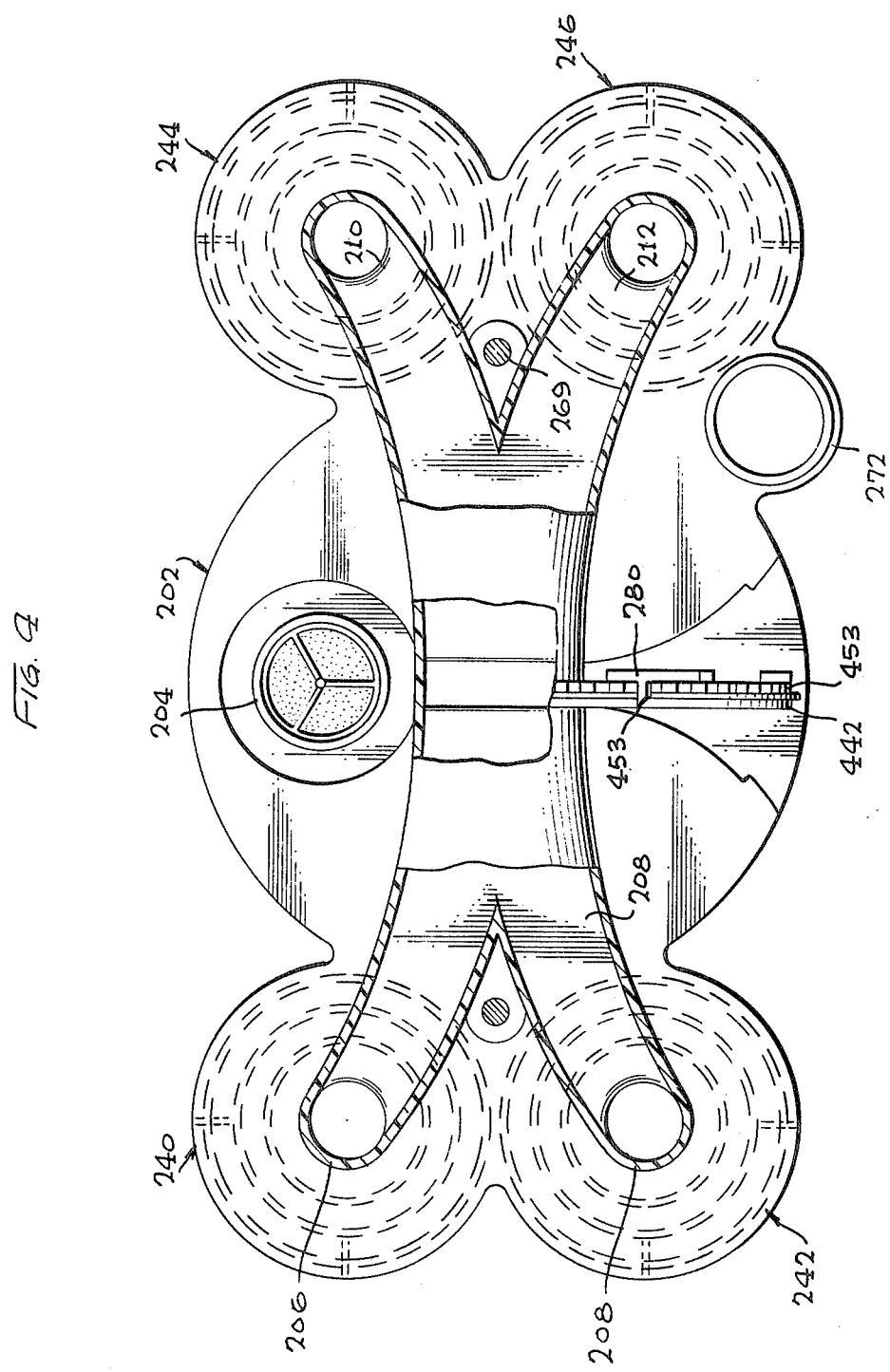

In order to more thoroughly understand the structure and flow patterns developed in the apparatus of FIGS. 2 and 3, attention is now directed to FIGS. 4–7 which illustrate the structural details of the apparatus in far greater detail. The apparatus will be explained in connection with the two operational phases, i.e., the user's expiration phase and inspiration phase. On expiration, of course, the user will create a positive pressure in both the inspiratory and expiratory tubes 11 and 12. On inspiration, the user will create a negative pressure in both the inspiratory and expiratory tubes 11 and 12.

Figure 7:
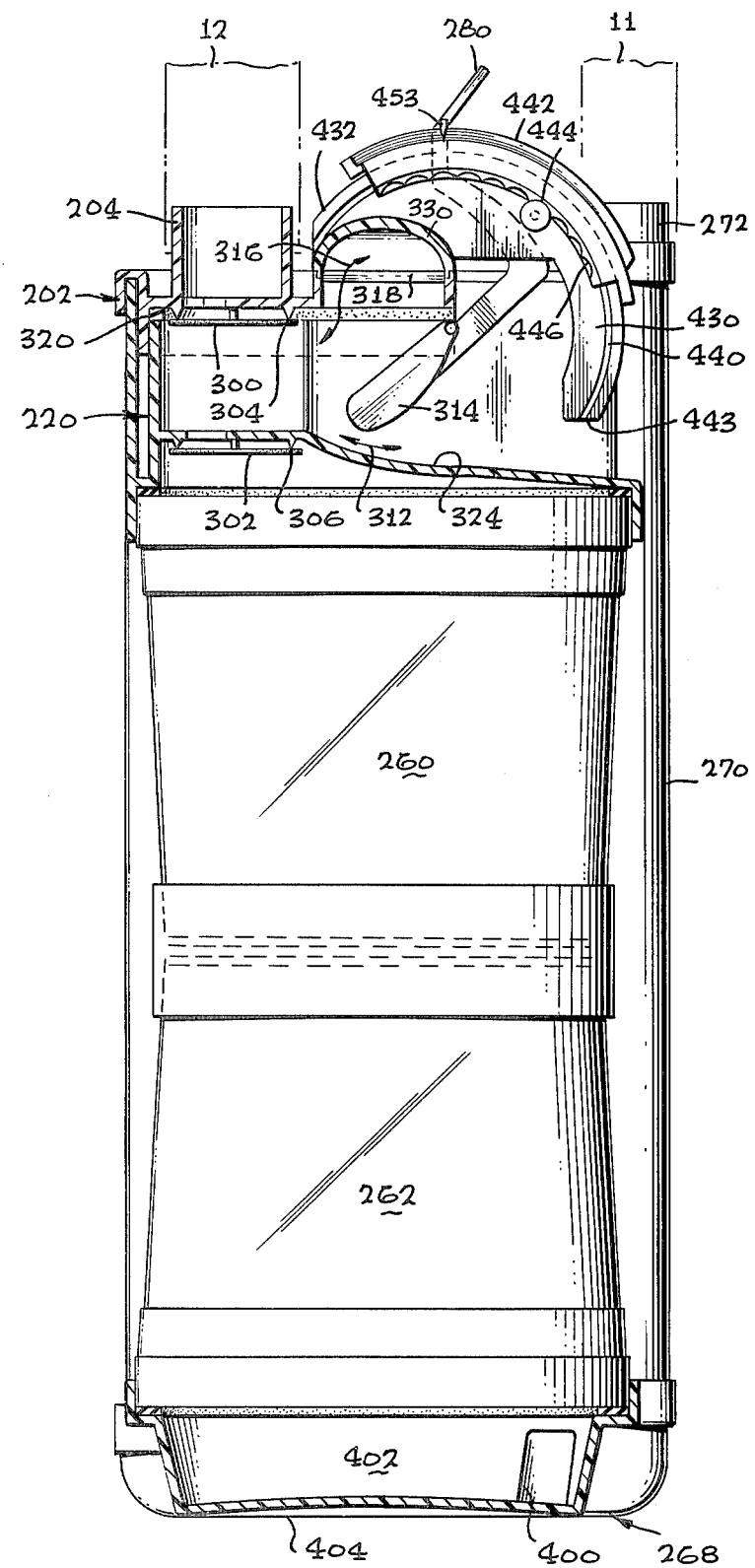
FIG. 7 is a side elevational view, partially broken away of the apparatus of FIG. 2.

The expiration phase will be considered initially. On expiration, the positive pressure created by the user in expiratory tube 12 will open the one-way expiratory valve 300 (FIG. 7) supported immediately adjacent nipple 204 in manifold sub-assembly 202. The positive pressure created during the expiration phase in inspiratory tube 11 will close the one-way inspiratory valve 302 (FIG. 7). It will be recognized that the expiratory and inspiratory valve elements 300 and 302 shown in FIG. 7 comprise centrally mounted disk members which in their normal state seal against knife-edge valve seats 304 and 306 respectively.

As a consequence of the positive pressure in expiratory tube 12, the user's expired air will flow past the opened expiratory element 300 into air mixing chamber 310 formed between manifold subassembly 202 and the air mixing chamber member 220. Two air flow exits are provided from the mixing chamber 310; namely, an air flow path 312 past proportioning valve member element 314 and an air flow path 316 past a knife-edge baffle 318 into the previously mentioned manifold passageways 206, 208, 210 and 212. Appropriate sealing 320 is provided to prevent any air escaping from the mixing chamber 310 through any path other than the previously mentioned paths 312 and 316.

In order to provide smooth non-turbulent air flow offering low back pressure or resistance to the user's expiration, the paths 312 and 316 are defined by appropriately radiused walls opening into increasingly larger cross-sectional areas. More particularly, initially consider flow path 312 which carries air from mixing chamber 310 to the environment. Note that air flow passage 312 is defined by a smoothly-radiused floor portion 324 extending between smoothly-radiused and outwardly-diverging walls 326 and 328 (FIG. 5). Similarly, the flow path 316 opens into previously mentioned manifold passageways 206, 208, 210 and 212 which are formed by a smoothly radiused wall 330 having a substantially semicircular cross section, which cross section is of increasing area extending outwardly from the baffle 318.

More will be said later herein about the structure and use of the proportioning valve element 314. Suffice it at this point to understand that its position determines the radio between the air flowing from mixing chamber 310 to the paths 312 and 316 (FIG. 7).

Figure 6:
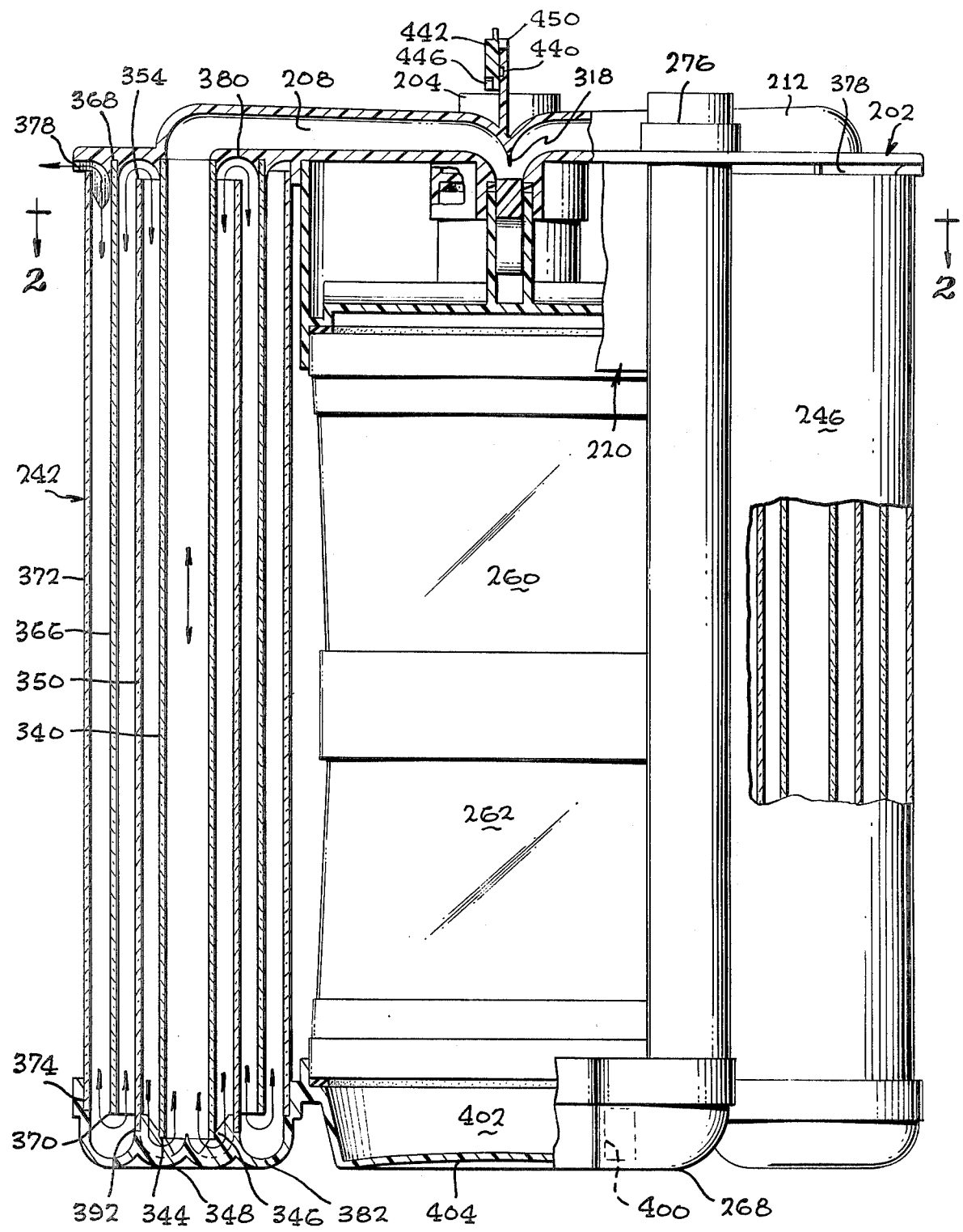
FIG. 6 is a front elevational view partially broken away of the apparatus of FIG. 2.

Reference was previously made to the reservoirs 240, 242, 244, and 246. These reservoirs are all identical in construction and are coupled in parallel fashion with respect to the air flow path. Reference will be made particularly to FIG. 6 to describe the structure of the reservoir 242. The reservoir 242 is comprised of a central tube 340 whose upper end is in communication with the open end of passageway 208. Thus, during the expiration phase, expired air flowing past baffle 318 via path 316 shown in FIG. 7 will flow through passageway 208 into the central tube 340 of reservoir 242. The lower end 344 of tube 340 is supported by radially spaced spacer elements 346 formed in a bowl portion 348 of the base member 268. The open lower end 344 of the tube 340 opens into a toroidal volume defined by tube 350 mounted concentrically about tube 340. Tube 350 defines an interior volume having a cross-sectional area which is larger than the cross-sectional area defined within the interior of tube 340. The lower end 352 of tube 350 is sealed so that air flowing from tube 340 into tube 350 will move up the tube as represented by the arrows to the open upper end 354. The upper end 354 of tube 350 is spaced from the undersurface of the manifold subassembly 202 so that air can flow out of tube 350 into a volume defined by tube 366. The volume defined by tube 366 has a cross-sectional area which is toroidally shaped and larger than the cross-sectional area of tube 350. Note that the upper end 368 of tube 366 is sealed to the underside of manifold subassembly 202 so that air flowing out of tube 350 flows downwardly through tube 366 exiting from the open bottom 370 thereof and then entering the outermost cylindrical tube 372. The lower end of tube 372 is sealed at 374 and the upper end opens to the environment through an overflow opening 378.

Thus, the reservoir 242 is defined by a central tube 340 and tubes 350, 366 and 372 which are concentrically mounted and of increasing diameter. The interior flow volumes defined by the tubes have cross-sectional areas of increasing dimension such that the expired air flowing into the open upper end of the central tube 340 is able to move down through the tube 340 and then traverse the succeeding path segments while experiencing relatively little resistance or back pressure. The dimensions between the walls of the tubes are selected to assure smooth non-turbulent substantially laminar flow so that air entering the reservoir from passageway 208 merely pushes the air already in the reservoir along without substantial mixing occurring at the boundary between the entering air and the air previously existing in the reservoir. This is important to assure that air expired by the user is stored in the reservoir such that during the immediately succeeding inspiration phase this same air is retrieved from the reservoir. Any air existing in the reservoir just prior to an expiration phase will be moved along the series path of flow segments defined by the concentric tubes and will then be exhausted through the overflow opening 378. To further assure smooth non-turbulent flow, the interior portions of the manifold subassembly 202 and bowl 348 of the base member 268 are radiused adjacent the open ends of the tubes as at 380 and 382.

During the inspiration phase, a negative pressure is created by the user in tubes 11 and 12. This negative pressure seals expiratory valve element 300 against valve seat 304 and opens valve element 302 displacing it from valve seat 306 (FIG. 7). The negative pressure is communicated to valve element 302 via previously-mentioned nipple 272 and tube 270. The lower end of tube 270 opens at 400 (FIG. 7) into an interior volume 402 of a central bowl 404 of the base member 268. The $CO_2$ absorber cannister 260 and 262 are supported above the interior volume 402. The cannisters 260 and 262 are substantially conventional and house $CO_2$ absorber material between upper and lower perforated plates 420. The perforations in the plates 420 are smaller than the size of the $CO_2$ absorber material granules 422. Thus, the negative pressure created during inspiration is transferred via tube 270, opening 400, and volume 402, through the cannisters 260 and 262 to open the one-way inspiratory check valve 302. As a consequence, air is drawn into the mixing chamber 310 via both air flow paths 312 and 316. Air drawn via path 312 comprises ambient air drawn from the environment. Air drawn via path 316 comprises air stored during the previous expiration phase in the manifold passageways and reservoirs. The amount of air drawn via path 312 from the environment is of course determined by the position of proportioning valve element 314.

The element 314 is pivotable between extreme clockwise and counter-clockwise positions (as viewed in FIG. 7). In the extreme counter clockwise position, the path 316 is fully open and the path 312 almost closed so that the user will breath mostly previously-expired air which of course will contain relatively little oxygen. By moving the valve element 314 to an extreme clockwise position, the path 316 will be substantially closed and the path 312 to the environment will be substantially open. It will of course be recognized that if the path 312 is fully open and the path 316 substantially closed, then the user will not rebreathe any expired air and will merely breathe the ambient air existing at the site the apparatus is being used. On the other than, with the path 312 almost closed, the user will be breathing mostly air which has been previously expired and stored. This expired air will of course have a very low oxygen content thus simulating a high elevated altitude, e.g., 19,000 feet above sea level. The amount of ambient air permitted to enter via path 312 when the valve element is in the extreme counter-clockwise position essentially determines the maximum altitude which can be simulated by an apparatus.

Although apparatus in accordance with the invention is conceptually capable of simulating virtually any elevated altitude, it is believed desirable to limit the maximum altitude to a level such as 19,000 feet above sea level. Accordingly, in the preferred embodiment of the invention disclosed herein, this limit is readily incorporated in the apparatus by assuring that when the proportioning valve member is in its extreme counter-clockwise position, as viewed in FIG. 7, the path 312 is still open to supply a proper amount of ambient air. Thus, by properly dimensioning the flow paths, the maximum altitude capable of being simulated is readily established. However, this assumes that the apparatus itself is being used at sea level. If in fact the apparatus is being used at an elevated altitude, for example at 7,500 feet where the $PO_2$ is only 75% of sea level, then of course the range of altitude simulated by the apparatus would be between 7,500 feet and some level considerably in excess of 19,000 feet. In recognition of the foregoing and in order to prevent the inadvertent simulation of levels above 19,000 feet, an adjustable limit stop means is incorporated in the preferred embodiment of the invention disclosed herein. More particularly, an arcuate support arm 430 has one end 432 secured to the manifold subassembly 202. The free end 433 extends between the radiused diverging walls 326 and 328 defined by the air mixing chamber member 220, terminating just above the floor 324. An arcuate slot 440 is formed in the arm 430, which slot serves as a track for an arcuate follower formed in a toothed rack 442. More particularly, the rack 442 is movable along the slot 440 defined in the support arm 430. The rack 442 can be fixed in any position along the arm 430 by a set screw 444 which cooperates with detents 446 formed in the inner surface of rack 442. Rack 442 carries a plurality of teeth 450 which define spaces 452 therebetween capable of receiving lug 453 on handle 280. Handle 280 is preferably integral with proportioning valve element 314 and is mounted for pivotal movement about pin 458.

The detents 446 are preferably calibrated in terms of the altitude at which the apparatus is being used. Thus, each detent may represent 2,000 feet of elevation such that if the apparatus is at sea level, the rack 442 is secured in one position along slot 440; if it is at 2,000 feet, the rack is secured in a second position; if it is at 4,000 feet, the rack is secured in a third position, etc. At each position of the rack, the handle 280 is positionable at any detent position 452 defined by teeth 450. When the rack is at the sea level position, the handle 280 can be moved through the full range defined by tooth 450 to thus enable porportioning valve element 314 to simulate any altitude between sea level and 19,000 feet. When the rack is at any other position, i.e. in a detent position associated with an above-sea-level altitude, the counter-clockwise pivotal movement (FIG. 7) of the handle 280 is limited to prevent the element 314 from moving to its extreme counter-clockwise position. More particularly, assume that the apparatus is at sea level and the rack 442 is properly positioned at the maximum counter-clockwise position (as seen in FIG. 7) along arm 430. In this position, the handle 280 can be pivoted to an extreme counter-clockwise position so that the apparatus is capable of simulating the maximum altitude of approximately 19,000 feet, for example. If the apparatus is being used at a higher altitude, the user should release the set screw 444 and then move the rack 442 in a clockwise direction along slot 440. This will of course reduce the range of counter-clockwise movement of the handle 280, and the amount the flow path 312 can be closed down, thus preventing the simulation of altitudes higher than approximately 19,000 feet.

Attention is now directed to FIG. 8 which illustrates in schematic form a further variation of the invention. FIG. 8 is substantially identical to FIG. 1 except for the inclusion of a by-pass flow path 500. The flow path 500 is coupled in parallel with the $CO_2$ absorber cannisters so as to enable a portion of the stored expired gas to be rebreathed without removing the carbon dioxide therefrom. In addition to the by-pass flow path 500, a proportioning valve element 502 is provided which is mounted for pivotal movement about a point 504 by handle 506. When in its extreme clockwise position, by-pass path 500 is closed.

When the by-pass path 500 is fully closed, then the apparatus in accordance with the invention operates as heretofore described. However, by adjusting the proportioning valve 502 so as to permit flow through the by-pass flow path 500, the carbon dioxide content of the inspired air can be increased. This capability is useful in certain medical applications where it is desired to assure that the $CO_2$ content of the user's inspired air remains at a certain level since the carbon dioxide content of the inspired air is the motivating factor in causing a user to continue to breathe.

From the foregoing, it should now be apparent that Applicant has disclosed herein an improved method and apparatus for supplying air to a user having a lower oxygen content than the ambient air. The improvements introduced in this application are primarily directed toward discouraging a user from inadvertently simulating a higher altitude than he is prepared for, enabling the user (or an attending nurse or physician) to regulate the carbon dioxide content of inspired air and to enhance the smoothness of air flow into and out of the reservoir and previously stored air.

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. Apparatus for supplying air, for inspiration by a user, having a lower oxygen concentration than the ambient air, said apparatus comprising:
    inspiratory path means having open first and second ends and including means therein for permitting air flow only in the direction from said second to said first end;
    expiratory path means having open first and second ends and including means therein for permitting air flow only in the direction from said first to said second end;
    air reservoir means;
    means coupling said expiratory path means second end to said reservoir means for supplying air thereto;
    means coupling said inspiratory path means second end to said ambient air and said reservoir means for drawing air therefrom comprising a selected ratio of ambient air and air from said reservoir means; and
    means for removing $CO_2$ from air flowing between said expiratory path means first end and said inspiratory path means first end, said $CO_2$ removing means including adjustable means for selectively varying the amount of $CO_2$ removed.

2. The apparatus of claim 1 wherein said means coupling said inspiratory path means second end includes means for establishing the ratio between air drawn from said ambient air and from said reservoir means; and
    adjustable limit means for adjusting the range over which said ratio can be established.

3. The apparatus of claim 1 wherein said means for removing $CO_2$ includes a $CO_2$ absorption air flow path and a by-pass air flow path coupled in parallel with said $CO_2$ absorption air flow path.

4. The apparatus of claim 3 wherein said adjustable means includes means for varying the ratio of air flowing through said $CO_2$ absorption path and said by-pass path.

5. Apparatus useful in an ambient air environment for supplying air for inspiration by a user, said apparatus including:
    source means for supplying air having a lower oxygen concentration than that of said ambient air, said source means including storage means for storing a quantity of air;
    means for combining a quantity of said air of lower oxygen concentration with a quantity of said ambient air in accordance with a selected ratio;
    means for supplying said combined air quantities to a user for inspiration;
    means for collecting air expired by a user for storage in said storage means; and
    means for controllably removing a selected amount of carbon dioxide from air supplied to said user for inspiration.

6. The apparatus of claim 5 wherein said means for combining includes means for selectively proportioning said quantities of lower oxygen air and ambient air.

7. The apparatus of claim 6 wherein said means for controllably removing carbon dioxide includes an absorption air flow path and a by-pass air flow path coupled in parallel with said absorption air flow path.

8. The apparatus of claim 7 further including adjustable means for varying the ratio of air flowing through said absorption path and said by-pass path.

9. A method of supplying air for inspiration by a user comprising the steps of:
    collecting a quantity of the user's expired air;
    combining said quantity of expired air with a quantity of ambient air in a selected ratio;
    supplying said combined air to said user; and
    removing a selected amount of carbon dioxide from the air supplied to said user.

10. Apparatus for supplying air for inspiration by a user having a lower oxygen concentration than the ambient air, said apparatus comprising:
    inspiratory path means having open first and second ends and including means therein for permitting air flow only in the direction from said second to said first end;
    expiratory path means having open first and second ends and including means therein for permitting air flow only in the direction from said first to said second end;
    reservoir means having an entrance opening;
    air mixing means defining first and second ports respectively communicating with said ambient air and said reservoir means entrance opening and a third port communicating with said inspiratory path second end and said expiratory path second end whereby a selected ratio of ambient air and air from said reservoir means is supplied to said inspiratory path means first end;
    means for removing carbon dioxide from the air supplied to said inspiratory path means first end;
    said air mixing means including adjustable valve means for varying the ratio of air flowing through said first and second ports; and
    adjustable limit means for limiting the range over which said valve means can vary said ratio.

11. The apparatus of claim 10 wherein said means for removing carbon dioxide includes adjustable means for varying the amount of carbon dioxide removed.

12. Apparatus for supplying air, for inspiration by a user, having a lower oxygen concentration than the ambient air, said apparatus comprising:
    inspiratory path means having open first and second ends and including means therein for permitting air flow only in the direction from said second to said first end;

expiratory path means having open first and second ends and including means therein for permitting air flow only in the direction from said first to said second end;

air reservoir means comprising a plurality of reservoir members each having an entrance opening;

a chamber member defining a mixing chamber open to the environment;

means coupling said expiratory path means second end to said mixing chamber for supplying air thereto;

manifold means defining multiple flow paths, each coupling said mixing chamber to a different one of said reservoir member entrance openings;

means coupling said inspiratory path means second end to said mixing chamber for drawing air therefrom comprising a selected ratio of ambient air from said environment and air from said reservoir members; and means for removing carbon dioxide from air flowing between said expiratory path means first end and said inspiratory path means first end.

13. The apparatus of claim 12 wherein each of said reservoir members has an overflow opening and wherein each reservoir member comprises:

a housing having a rigid outer wall and including baffle means therein for defining a plurality of flow path segments communicating with one another to form a series flow path extending from said entrance opening to said overflow opening, said segments in said series flow path being of increasing cross-sectional area to minimize resistance to air flow from said entrance opening to said overflow opening.

14. The reservoir of claim 13 wherein said housing includes spaced first and second surface; and wherein said baffle means includes first and second concentric cylindrical walls extending from said first surface toward said second surface but spaced therefrom and third and fourth concentric cylindrical walls extending from said second surface toward said first surface but spaced therefrom, said cylindrical walls extending from said first surface being interleaved with said cylindrical walls extending from said second surface to define a first path segment between said first and third cylindrical walls, a second path segment between said third and second cylindrical walls and a third path segment between said second and fourth cylindrical walls.

15. The apparatus of claim 12 wherein said means for removing carbon dioxide includes adjustable means for varying the amount of carbon dioxide removed.

16. The apparatus of claim 12 including manually controllable proportioning valve means for varying said ratio of ambient air and air from said reservoir members.

17. The apparatus of claim 16 including adjustable means for adjusting the range over which said ratio can be varied.

* * * * *